US011602316B2

United States Patent
Berner et al.

(10) Patent No.: US 11,602,316 B2
(45) Date of Patent: Mar. 14, 2023

(54) METHOD FOR CAPTURING PROJECTION DATA BY WAY OF A COMPUTED TOMOGRAPHY DEVICE AND COMPUTED TOMOGRAPHY DEVICE

(71) Applicant: Siemens Healthcare GmbH, Erlangen (DE)

(72) Inventors: Matthias Berner, Herzogenaurach (DE); Ulrich Kuehn, Baiersdorf (DE); Maurizio Bianconi, Munich (DE)

(73) Assignee: Siemens Healthcare GmbH, Erlangen (DE)

( * ) Notice: Subject to any disclaimer, the term of this patent is extended or adjusted under 35 U.S.C. 154(b) by 269 days.

(21) Appl. No.: 17/014,008

(22) Filed: Sep. 8, 2020

(65) Prior Publication Data

US 2021/0077039 A1 Mar. 18, 2021

(30) Foreign Application Priority Data

Sep. 17, 2019 (EP) ..................................... 19197797

(51) Int. Cl.
*A61B 6/00* (2006.01)
*A61B 6/03* (2006.01)
*A61B 6/06* (2006.01)

(52) U.S. Cl.
CPC ............ *A61B 6/4078* (2013.01); *A61B 6/032* (2013.01); *A61B 6/06* (2013.01)

(58) Field of Classification Search
CPC ......... A61B 6/4078; A61B 6/032; A61B 6/06; A61B 6/0407; A61B 6/54
See application file for complete search history.

(56) References Cited

U.S. PATENT DOCUMENTS

2012/0128120 A1* 5/2012 De Man .................... A61B 6/08
378/16
2013/0308747 A1 11/2013 Abraham et al.

OTHER PUBLICATIONS

Xia Van et al: "Dose reduction achieved by dynamically collimating the redundant rays in fan-beam and cone-beam CT", 2013 IEEE Nuclear Science Symposium and Medical Imaging Conference (2013 NSS/MIC), IEEE, pp. 1-4, XP032601595, DOI: 10.1109/NSSMIC.2013.6829341; [gefunden am Jun. 10, 2014]; Abstract; Figures 1-7; paragraphs I-III; 2013.
Extended European Search Report for European Application No. 19197797.4 dated Jan. 2, 2020.

* cited by examiner

*Primary Examiner* — Courtney D Thomas
(74) *Attorney, Agent, or Firm* — Harness, Dickey & Pierce, P.L.C.

(57) ABSTRACT

A method is for capturing projection data. The method includes positioning the first diaphragm jaw and a second diaphragm jaw to set a layer collimation of a fan beam of radiation via the first diaphragm jaw and the second diaphragm jaw; capturing projection data of a region of a patient to be imaged via a detector and radiation source rotated in a plane of rotation, moving the region of the patient to be imaged relative to the plane of rotation, the fan beam penetrating the region of the patient to be imaged and striking the detector; and moving at least one of the first and second diaphragm jaw during the capturing, to dynamically adjust a position of a boundary surface of the fan beam to a position of a boundary surface of the region, to avoid the fan beam penetrating the patient outside the region to be imaged.

21 Claims, 3 Drawing Sheets

METHOD FOR CAPTURING PROJECTION DATA BY WAY OF A COMPUTED TOMOGRAPHY DEVICE AND COMPUTED TOMOGRAPHY DEVICE

PRIORITY STATEMENT

The present application hereby claims priority under 35 U.S.C. § 119 to European patent application number EP 19197797.4 filed Sep. 17, 2019, the entire contents of which are hereby incorporated herein by reference.

FIELD

Various example embodiments of the invention generally relate to a method for capturing projection data by way of a computed tomography device and/or to a computed tomography device.

BACKGROUND

In computed tomography, in particular in the case of a short spiral scan with high Z-coverage, a large dose can be avoided by way of dynamic collimation. At the beginning and/or at the end of the spiral scan, by way of a diaphragm, a position of a boundary surface of a fan beam is dynamically adjusted to a position of a boundary surface of an area of the patient to be imaged in order to avoid the fan beam penetrating the patient outside the area to be imaged.

A high dynamic performance is required for this purpose, in particular, in the case of a high couch pitch. On the other hand, high positioning accuracy is required for the layer collimation of the fan beam. In addition to the conventional collimator, which is provided for the layer collimation of the fan beam and is not designed for the high speeds which are required for dynamic collimation, a conventional computed tomography device therefore has a further shutter system which is specially designed for dynamic collimation. This further shutter system is also referred to as a shutter unit.

Thus, with the conventional collimator and the shutter unit, two separate shutter systems have been used side by side, as a result of which the variance, the complexity and the costs are increased.

SUMMARY

At least one embodiment of the invention provides an alternative to the conventional collimation of a fan beam which is improved with regard to the complexity of the mechanical construction. Further advantageous aspects of the invention are taken into account in the claims.

At least one embodiment of the invention relates to a method for capturing projection data by way of a computed tomography device which has a radiation source for generating radiation, a detector and a collimator having a first diaphragm jaw and a second diaphragm jaw, the method comprising:

positioning the first diaphragm jaw and positioning the second diaphragm jaw in such a way that a layer collimation of a fan beam of the radiation is adjusted by way of the first diaphragm jaw and the second diaphragm jaw;

capturing the projection data of a region of a patient to be imaged via the detector, while the detector and the radiation source are rotated in a plane of rotation about an axis of rotation and at the same time the region of the patient to be imaged is moved relative to the plane of rotation, the fan beam penetrating the region of the patient to be imaged and striking the detector; and moving the first diaphragm jaw and/or moving the second diaphragm jaw during the capturing of the projection data in such a way that a position of a boundary surface of the fan beam is dynamically adjusted to a position of a boundary surface of the region of the patient to be imaged, such that the fan beam penetrating the patient outside the region to be imaged is essentially avoided, in particular is avoided, wherein in particular the position of the boundary surface of the region of the patient to be imaged changes as a result of the movement of the region of the patient to be imaged relative to the plane of rotation.

According to one embodiment, the invention furthermore relates to a computed tomography device, comprising:
a radiation source for generating radiation,
a detector and
a collimator with a first diaphragm jaw and a second diaphragm jaw,
wherein the collimator is designed to position the first diaphragm jaw and to position the second diaphragm jaw in such a way that a layer collimation of a fan beam of the radiation can be adjusted by way of the first diaphragm jaw and of the second diaphragm jaw,
wherein the detector is designed to capture the projection data of a region of a patient to be imaged, while the detector and the radiation source are rotated in a plane of rotation about an axis of rotation and at the same time the region of the patient to be imaged is moved relative to the plane of rotation, wherein the fan beam penetrates the region of the patient to be imaged and strikes the detector,
wherein the collimator is furthermore designed to move the first diaphragm jaw and/or to move the second diaphragm jaw during the capturing of the projection data in such a way that a position of a boundary surface of the fan beam can be dynamically adjusted to a position of a boundary surface of the region of the patient to be imaged, such that the fan beam penetrating the patient outside the region to be imaged can be essentially avoided, in particular avoided, wherein in particular, the position of the boundary surface of the region of the patient to be imaged changes as a result of the movement of the region of the patient to be imaged relative to the plane of rotation.

According to one embodiment, the invention furthermore relates to a method for capturing projection data by way of a computed tomography device, the computed tomography device including a radiation source for generating radiation, a detector and a collimator including a first diaphragm jaw and a second diaphragm jaw, the method comprising:

positioning the first diaphragm jaw and positioning the second diaphragm jaw to set a layer collimation of a fan beam of the radiation via the first diaphragm jaw and the second diaphragm jaw;

capturing projection data of a region of a patient to be imaged via the detector, while the detector and the radiation source are rotated in a plane of rotation about an axis of rotation and at a same time, moving the region of the patient to be imaged relative to the plane of rotation, wherein the fan beam penetrates the region of the patient to be imaged and strikes the detector; and moving at least one of the first diaphragm jaw and the second diaphragm jaw during the capturing of the projection data, to dynamically adjust a position of a boundary surface of the fan beam to a position of a boundary surface of the region of the patient to be imaged, such that outside the region to be imaged, penetration of the patient by the fan beam is essentially avoided.

According to one embodiment, the invention furthermore relates to a computed tomography device, comprising:

a radiation source to generate radiation;

a detector; and a collimator including a first diaphragm jaw and a second diaphragm jaw, wherein the collimator is designed to position the first diaphragm jaw and is designed to position the second diaphragm jaw, the first diaphragm jaw and the second diaphragm jaw being configurable to set a layer collimation of a fan beam of the radiation, wherein the detector is designed to capture projection data of a region of a patient to be imaged, while the detector and the radiation source are rotated in a plane of rotation about an axis of rotation and at a same time, the region of the patient to be imaged is moved relative to the plane of rotation, wherein the fan beam is configured to penetrate the region of the patient to be imaged and strike the detector, and wherein the collimator is designed to move at least one of the first diaphragm jaw and the second diaphragm jaw during the capture of the projection data to dynamically adjust a position of a boundary surface of the fan beam to a position of a boundary surface of the region of the patient to be imaged, such that outside the region to be imaged, penetration of the patient by the fan beam is essentially avoided.

BRIEF DESCRIPTION OF THE DRAWINGS

The invention is explained in more detail hereinafter on the basis of example embodiments with reference to the attached figures. The representation in the figures is schematic, greatly simplified and not necessarily to scale.

In the figures.

DETAILED DESCRIPTION OF THE EXAMPLE EMBODIMENTS

The above and other elements, features, steps, and concepts of the present disclosure will be more apparent from the following detailed description in accordance with example embodiments of the invention, which will be explained with reference to the accompanying drawings.

Some examples of the present disclosure generally provide for a plurality of circuits, data storages, connections, or electrical devices such as e.g. processors. All references to these entities, or other electrical devices, or the functionality provided by each, are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

It is to be understood that the following description of embodiments is not to be taken in a limiting sense. The scope of the invention is not intended to be limited by the embodiments described hereinafter or by the drawings, which are taken to be illustrative only.

The drawings are to be regarded as being schematic representations, and elements illustrated in the drawings are not necessarily shown to scale. Rather, the various elements are represented such that their function and general purpose become apparent to a person skilled in the art. Any connection, or communication, or coupling between functional blocks, devices, components, or other physical or functional units shown in the drawings or described herein may also be implemented by an indirect connection or coupling. A communication between devices may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/ DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for capturing projection data by way of a computed tomography device which has a radiation source for generating radiation, a detector and a collimator having a first diaphragm jaw and a second diaphragm jaw, the method comprising:

positioning the first diaphragm jaw and positioning the second diaphragm jaw in such a way that a layer collimation of a fan beam of the radiation is adjusted by way of the first diaphragm jaw and the second diaphragm jaw;

capturing the projection data of a region of a patient to be imaged via the detector, while the detector and the radiation source are rotated in a plane of rotation about an axis of rotation and at the same time the region of the patient to be imaged is moved relative to the plane of rotation, the fan beam penetrating the region of the patient to be imaged and striking the detector; and moving the first diaphragm jaw and/or moving the second diaphragm jaw during the capturing of the projection data in such a way that a position of a boundary surface of the fan beam is dynamically adjusted to a position of a boundary surface of the region of the patient to be imaged, such that the fan beam penetrating the patient outside the region to be imaged is essentially avoided, in particular is avoided, wherein in particular the position of the boundary surface of the region of the patient to be imaged changes as a result of the movement of the region of the patient to be imaged relative to the plane of rotation.

In this way, the layer collimation and the dynamic collimation can be effected by way of the same diaphragm jaws. The additional shutter unit can thus be dispensed with, as a result of which the variance, the complexity and the costs for hardware and assembly can be reduced.

According to one embodiment, when the projection data is captured, the layer collimation of the fan beam of the radiation is kept constant for at least one half revolution, for example, for at least one full revolution, of the detector and the radiation source about the axis of rotation. In particular, it can be provided that for the at least one half revolution, for example for the at least one full revolution, the position of the first diaphragm jaw is kept constant and/or the position of the second diaphragm jaw is kept constant.

The projection data can be, for example, projection data for a multi-layer computed tomography imaging examination, which is also known to a person skilled in the art as a multi-slice computed tomography imaging examination.

The layer collimation of the fan beam of the radiation can be adjusted, for example, by masking portions of the radiation which are aligned with regions of the detector, in particular slices of the detector, which are not selected for the multi-layer computed tomography imaging examination, by way of the first diaphragm jaw and the second diaphragm jaw.

According to one embodiment, the position of the boundary surface of the fan beam is dynamically adjusted to the position of the boundary surface of the region of the patient to be imaged until the fan beam is completely masked by the first diaphragm jaw and the second diaphragm jaw.

According to one embodiment, moving the first diaphragm jaw and/or moving the second diaphragm jaw in each case takes place at a speed, for example, a speed relative to and/or perpendicular to the plane of rotation, of at least 150 millimeters per second, in particular, at least 175 millimeters per second, for example, at least 200 millimeters per second, in particular in order to dynamically adjust the position of the boundary surface of the fan beam to the position of the boundary surface of the region to be imaged.

According to one embodiment, moving the first diaphragm jaw and/or moving the second diaphragm jaw in each case comprises an acceleration, for example, an acceleration relative to and/or perpendicular to the plane of rotation, of at least 3000 millimeters per square second, in particular at least 3500 millimeters per square second, for example, at least 4000 millimeters per square second, in particular in order to dynamically adjust the position of the boundary surface of the fan beam to the position of the boundary surface of the region to be imaged.

The first diaphragm jaw can be positioned, for example, by converting a first rotational movement of a first threaded spindle into a first translational movement of the first diaphragm jaw via a first threaded drive. The first diaphragm jaw can be moved, for example, by converting a second rotational movement of the first threaded spindle into a second translational movement of the first diaphragm jaw via the first threaded drive, in particular, in order to dynamically adjust the position of the boundary surface of the fan beam to the position of the boundary surface of the region to be imaged.

The second diaphragm jaw can be positioned, for example, by converting a first rotational movement of a second threaded spindle into a first translational movement of the second diaphragm jaw via a second threaded drive. The second diaphragm jaw can be moved, for example, by converting a second rotational movement of the second threaded spindle into a second translational movement of the second diaphragm jaw via the second threaded drive, in particular, in order to dynamically adjust the position of the boundary surface of the fan beam to the position of the boundary surface of the region to be imaged.

The first translational movement of the first diaphragm jaw and the second translational movement of the first diaphragm jaw can take place, for example, parallel to the axis of rotation in each case. The first translational movement of the second diaphragm jaw and the second translational movement of the second diaphragm jaw can take place, for example, parallel to the axis of rotation in each case.

According to one embodiment, the first rotational movement of the first threaded spindle and the second rotational movement of the first threaded spindle are driven via a first stepper motor and/or the first rotational movement of the second threaded spindle and the second rotational movement of the second threaded spindle are driven via a second stepper motor.

According to one embodiment, the second rotational movement of the first threaded spindle is controlled in a field-oriented manner and/or the second rotational movement of the second threaded spindle is controlled in a field-oriented manner. According to one embodiment, the first rotational movement of the first threaded spindle is controlled in a field-oriented manner and/or the first rotational movement of the second threaded spindle is controlled in a field-oriented manner.

According to one embodiment, the invention furthermore relates to a computed tomography device, comprising:
a radiation source for generating radiation,
a detector and a collimator with a first diaphragm jaw and a second diaphragm jaw, wherein the collimator is designed to position the first diaphragm jaw and to position the second diaphragm jaw in such a way that a layer collimation of a fan beam of the radiation can be adjusted by way of the first diaphragm jaw and of the second diaphragm jaw, wherein the detector is designed to capture the projection data of a region of a patient to be imaged, while the detector and the radiation source are rotated in a plane of rotation about an axis of rotation and at the same time the region of the patient to be imaged is moved relative to the plane of rotation, wherein the fan beam penetrates the region of the patient to be imaged and strikes the detector, wherein the collimator is furthermore designed to move the first diaphragm jaw and/or to move the second diaphragm jaw during the capturing of the projection data in such a way that a position of a boundary surface of the fan beam can be dynamically adjusted to a position of a boundary surface of the region of the patient to be imaged, such that the fan beam penetrating the patient outside the region to be imaged can be essentially avoided, in particular avoided, wherein in particular, the position of the boundary surface of the region of the patient to be imaged changes as a result of the movement of the region of the patient to be imaged relative to the plane of rotation.

According to one embodiment, the collimator is designed to keep the layer collimation of the fan beam of the radiation constant for at least one half revolution, for example, for at least one full revolution, of the detector and of the radiation source about the axis of rotation during the capturing of the projection data. In particular, it can be provided that the collimator is designed to keep the position of the first diaphragm jaw constant and/or to keep the position of the second diaphragm jaw constant for the at least one half revolution, for example for the at least one full revolution.

According to one embodiment, the collimator is designed to dynamically adjust the position of the boundary surface of the fan beam to the position of the boundary surface of the region of the patient to be imaged until the fan beam is completely masked by the first diaphragm jaw and the second diaphragm jaw.

According to one embodiment, the collimator is designed to move the first diaphragm jaw and/or the second diaphragm jaw in each case at a speed, for example, a speed relative and/or perpendicular to the plane of rotation, of at least 150 millimeters per second, in particular, at least 175 millimeters per second, for example, at least 200 millimeters per second, in particular to dynamically adjust the position of the boundary surface of the fan beam to the position of the boundary surface of the region to be imaged.

According to one embodiment, the collimator is designed to move the first diaphragm jaw and/or the second diaphragm jaw in each case at an acceleration, for example, an acceleration relative and/or perpendicular to the plane of rotation, of at least 3000 millimeters per square second, in particular at least 3500 millimeters per square second, for example at least 4000 millimeters per square second, in particular to dynamically adjust the position of the boundary surface of the fan beam to the position of the boundary surface of the region to be imaged.

According to one embodiment, the collimator comprises a first threaded spindle and a first threaded drive, wherein the first threaded drive is designed to convert a first rotational movement of the first threaded spindle into a first translational movement of the first diaphragm jaw, by which the positioning of the first diaphragm jaw takes place, and/or to convert a second rotational movement of the first threaded spindle into a second translational movement of the first diaphragm jaw, by which the movement of the first diaphragm jaw takes place.

According to one embodiment, the collimator comprises a second threaded spindle and a second threaded drive, wherein the second threaded drive is designed to convert a first rotational movement of the second threaded spindle into a first translational movement of the second diaphragm jaw, by which the positioning of the second diaphragm jaw takes place, and/or to convert a second rotational movement of the second threaded spindle into a second translational movement of the second diaphragm jaw, by which the movement of the second diaphragm jaw takes place.

According to one embodiment, a thread pitch of the first threaded spindle is at least 3 millimeters per revolution, in particular, at least 3.5 millimeters per revolution, for example, at least 4 millimeters per revolution, and/or a thread pitch of the second threaded spindle is at least 3 millimeters per revolution, in particular, at least 3.5 millimeters per revolution, for example, at least 4 millimeters per revolution.

According to one embodiment, the collimator has a first stepper motor for driving the first rotational movement of the first threaded spindle and the second rotational movement of the first threaded spindle and/or the collimator has a second stepper motor for driving the first rotational movement of the second threaded spindle and the second rotational movement of the second threaded spindle.

According to one embodiment, the computed tomography device also has a control unit which is designed for field-oriented control of the second rotational movement of the first threaded spindle and/or for field-oriented control of the second rotational movement of the second threaded spindle.

According to one embodiment, the control unit is designed for field-oriented control of the first rotational movement of the first threaded spindle and/or for field-oriented control of the first rotational movement of the second threaded spindle.

The control unit can, for example, comprise at least one Field Programmable Gate Array (FPGA). Field-oriented control can be implemented, in particular, in the Field Programmable Gate Array (FPGA).

As a result, it is possible, on the one hand to achieve a high speed for moving the diaphragm jaws and on the other hand, a high positioning accuracy for positioning the diaphragm jaws.

Within the scope of the invention, features described with regard to different embodiments of the invention and/or different claim categories (method, use, apparatus, system, arrangement, etc.) may be combined into further embodiments of the invention. For example, a claim relating to an apparatus may also be developed with features described or claimed in connection with a method, and vice versa. Functional features of a method can be carried out by correspondingly designed physical components. In addition to the embodiments of the invention which are explicitly described in this application, various further embodiments of the invention are conceivable, which are available to a person skilled in the art without departing from the scope of the invention which is specified by the claims.

The use of the indefinite article "a" or "an" does not exclude the possibility that the feature concerned may also be present multiple times. The use of the term "have" does not exclude the possibility that the terms associated with the term "have" may be identical. For example, the computed tomography device has the computed tomography device.

The use of the term "unit" does not exclude the possibility that the object to which the term "unit" relates may have multiple components which are spatially separated from one another.

Figure 1:
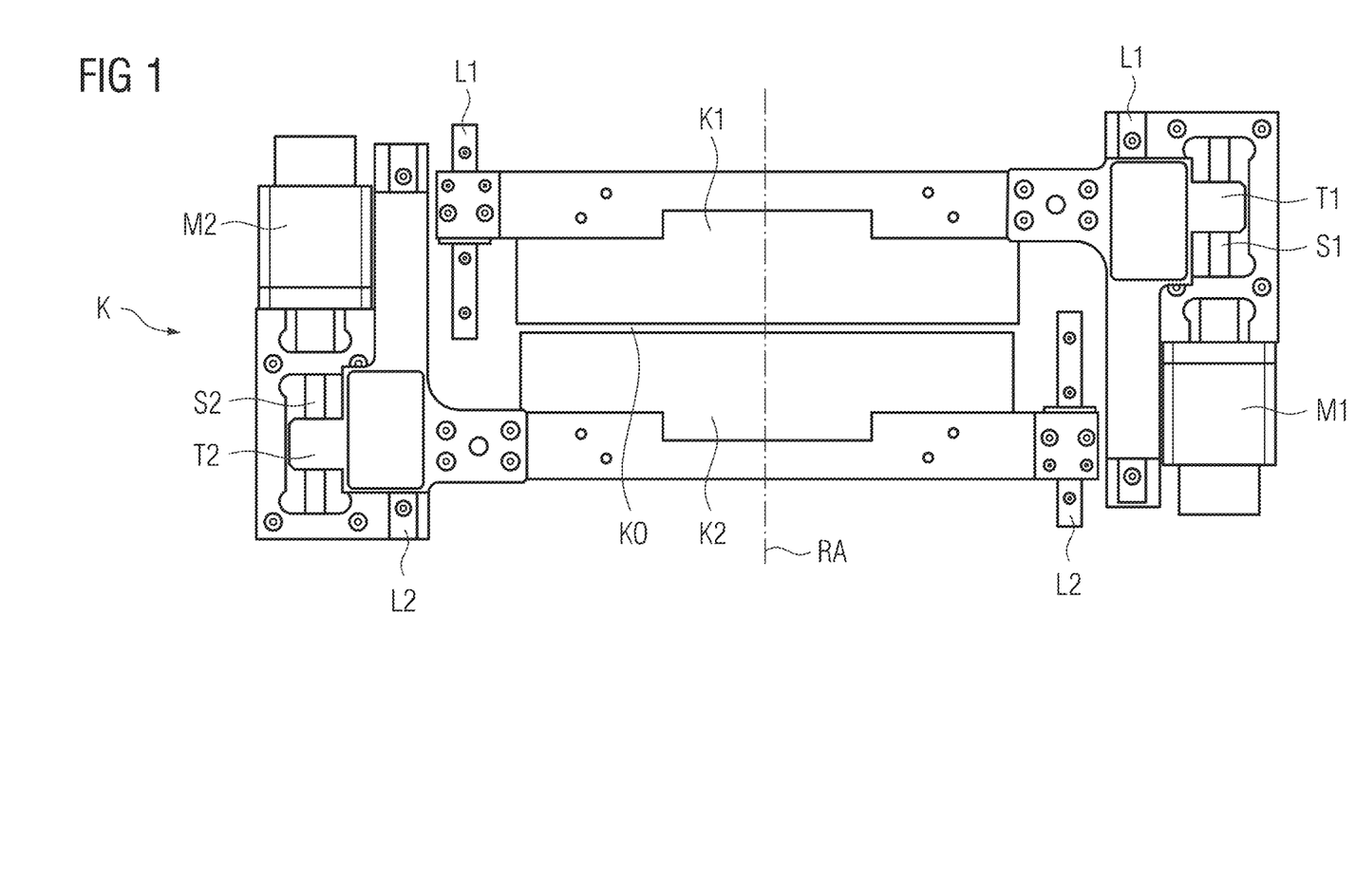
FIG. 1 shows a collimator.

FIG. 1 shows the collimator K with the first diaphragm jaw K1 and the second diaphragm jaw K2. The first diaphragm jaw is mounted in the first rail guide L1. The second diaphragm jaw is mounted in the second rail guide L2. The first diaphragm jaw K1 and the second diaphragm jaw K2 are each curved in design and arranged coaxially to one another. The second diaphragm jaw K2 has a smaller radius of curvature than the first diaphragm jaw K1, enabling the first diaphragm jaw K1 and the second diaphragm jaw K2 to be arranged at least partially overlapping from the perspective of the radiation source 26.

The collimator K has the first threaded spindle S1 and the first threaded drive T1, wherein the first threaded drive T1 is designed to convert a first rotational movement of the first threaded spindle S1 into a first translational movement of the first diaphragm jaw K1, by which the positioning PK1 of the first diaphragm jaw K1 takes place, and to convert a second rotational movement of the first threaded spindle S1 into a second translational movement of the first diaphragm jaw K1, by which the movement BK1 of the first diaphragm jaw K1 takes place.

The collimator K comprises the second threaded spindle S2 and the second threaded drive T2, wherein the second threaded drive T2 is designed to convert a first rotational movement of the second threaded spindle S2 into a first translational movement of the second diaphragm jaw K2, by which the positioning PK2 of the second diaphragm jaw K2 takes place, and to convert a second rotational movement of the second threaded spindle S2 into a second translational movement of the second diaphragm jaw K2, by which the movement BK2 of the second diaphragm jaw K2 takes place.

The collimator K includes the first stepper motor M1 for driving the first rotational movement of the first threaded spindle S1 and the second rotational movement of the first threaded spindle S1. The collimator K includes the second stepper motor M2 for driving the first rotational movement of the second threaded spindle S2 and the second rotational movement of the second threaded spindle S2.

Figure 2:
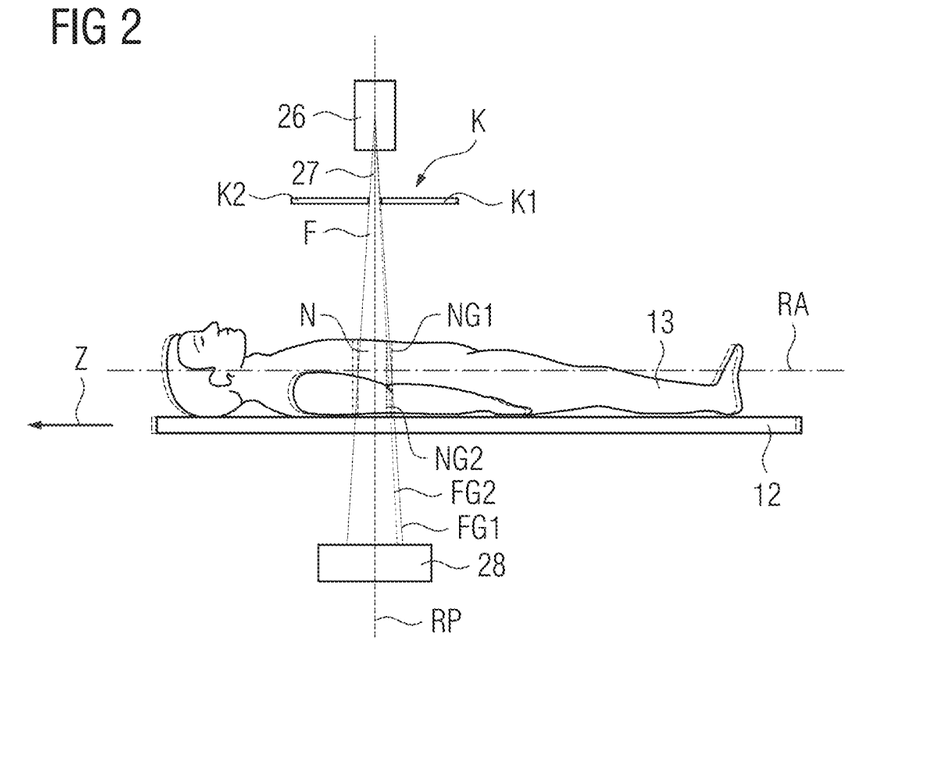
FIG. 2 shows a representation of a multi-layer computed tomography imaging examination of a patient using the collimator.

FIG. 2 shows a representation of a multi-layer computed tomography imaging examination of the patient 13 using the collimator K.

The collimator K is designed to position PK1 the first diaphragm jaw K1 and to position PK2 the second diaphragm jaw K2 in such a way that a layer collimation of the fan beam F of the radiation 27 can be adjusted by way of the first diaphragm jaw K1 and the second diaphragm jaw K2. A portion of the radiation 27 penetrates through the collimator gap K0 which is formed between the first diaphragm jaw K1 and the second diaphragm jaw K2.

The detector 28 is designed to capture ED the projection data of a region N of a patient 13 to be imaged, while the detector 28 and the radiation source 26 are rotated in a plane of rotation RP about the axis of rotation RA and at the same time the region N of the patient 13 to be imaged is moved relative to the plane of rotation RP, the fan beam F penetrating the region N of the patient 13 to be imaged and striking the detector 28.

The collimator K is furthermore designed to move BK1 the first diaphragm jaw K1 and/or to move BK2 the second diaphragm jaw K2 during the capturing ED of the projection data in such a way that a position of a boundary surface of the fan beam F can be dynamically adjusted to a position of a boundary surface of the region N of the patient 13 to be imaged, the fan beam F penetrating the patient 13 outside the region to be imaged N thus being essentially avoided.

The patient 13 and thus their region N to be imaged are moved via the patient positioning apparatus 10 in the direction Z, which is parallel to the axis of rotation RA. As a result of the movement of the region N of the patient 13 to be imaged relative to the plane of rotation RP, the position of the boundary surface of the region N of the patient 13 to be imaged changes from the position NG1 to the position NG2.

As a result of the movement of the first diaphragm jaw K1 in the direction Z, the position of the boundary surface of the fan beam F changes from the position FG1 to the position FG2. In this case, a portion of the radiation 27, which was still part of the fan beam F in the position FG1, is masked by the first diaphragm jaw K1, this portion of the radiation 27 in the position FG2 no longer being part of the fan beam F. If this portion of the radiation 27 is not masked, it penetrates the patient 13 outside the region to be imaged N if its boundary surface is in the position NG2.

When capturing ED the projection data, the collimator K is designed to keep the layer collimation of the fan beam F of the radiation 27 constant for at least one half revolution of the detector 28 and the radiation source 26 about the axis of rotation RA.

The collimator K is designed to dynamically adjust the position of the boundary surface FG of the fan beam F to the position of the boundary surface NG of the region N of the patient 13 to be imaged until the fan beam F is completely masked by the first diaphragm jaw K1 and the second diaphragm jaw K2, for example, due to a complete closing of the collimator gap K0. The closing of the collimator gap K0 can take place, in particular, synchronously with a final section of the spiral scan.

Figure 3:
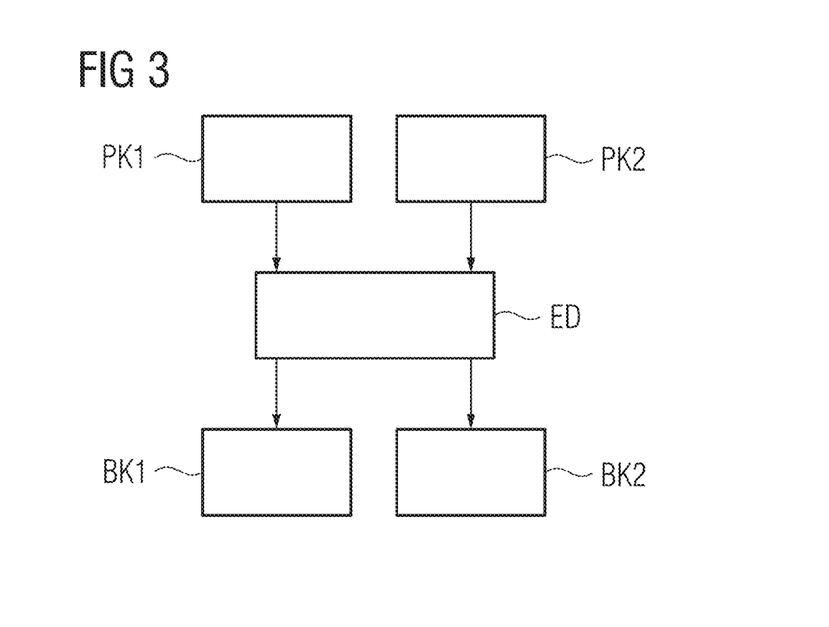
FIG. 3 shows a flow chart of a method for capturing projection data via a computed tomography device.

FIG. 3 shows a flow chart of a method for capturing projection data via the computed tomography device 1, which has the radiation source 26 for generating the radiation 27, the detector 28 and the collimator K with the first diaphragm jaw K1 and the second diaphragm jaw K2, the method comprising:

positioning PK1 of the first diaphragm jaw K1 and positioning PK2 of the second diaphragm jaw K2 in such a way that a layer collimation of the fan beam F of the radiation 27 is adjusted by way of the first diaphragm jaw K1 and the second diaphragm jaw K2, capturing ED the projection data of the region N of the patient 13 to be imaged via the detector 28, while the detector 28 and the radiation source 26 are rotated in the plane of rotation RP about the axis of rotation RA and at the same time the region N of the patient 13 to be imaged is moved relative to the plane of rotation RP, the fan beam F penetrating the region N of the patient 13 to be imaged and striking the detector 28, and moving BK1 the first diaphragm jaw K1 and/or moving BK2 the second diaphragm jaw K2 during the capturing ED of the projection data in such a way that a position FG1, FG2 of a boundary surface of the fan beam F is dynamically adjusted to a position NG1, NG2 of a boundary surface of the region N of the patient 13 to be imaged, such that the fan beam F penetrating the patient 13 outside the region to be imaged N is essentially avoided.

Figure 4:
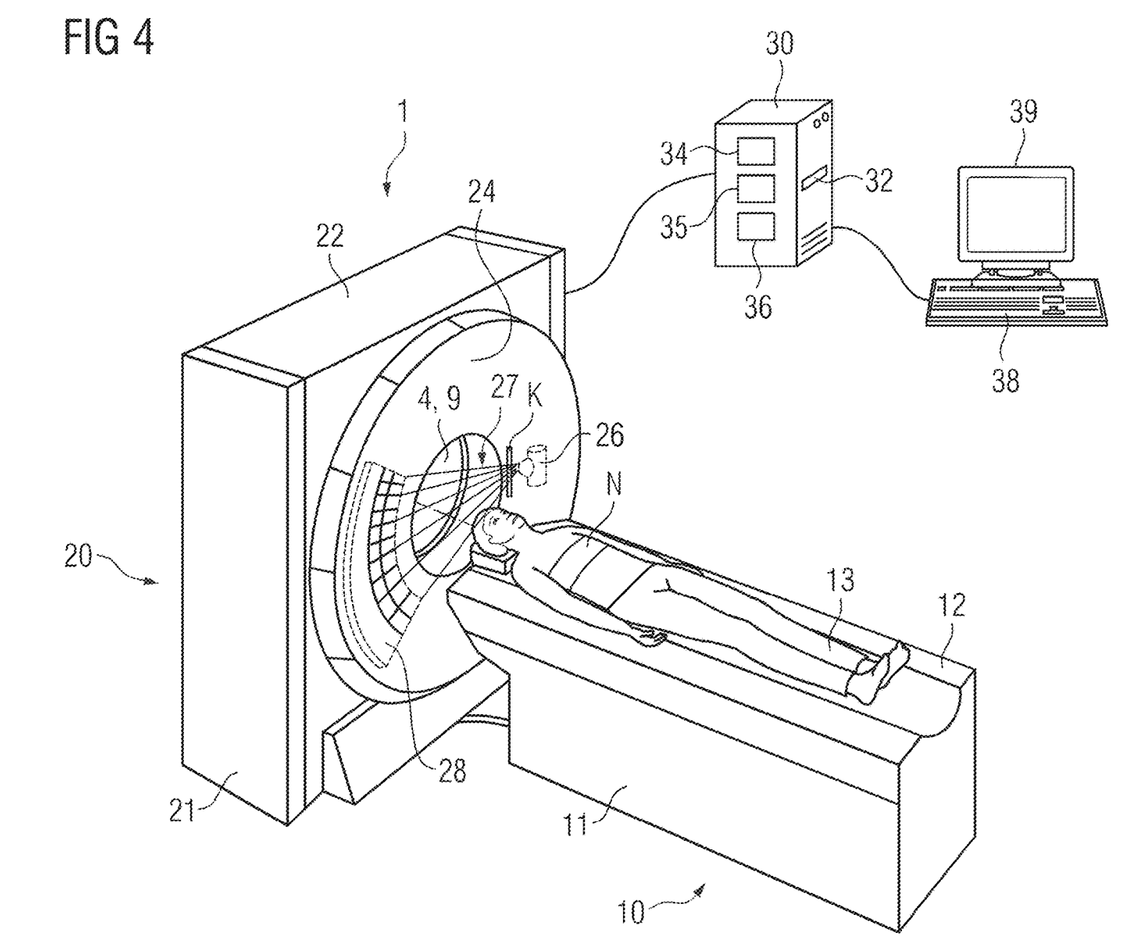
FIG. 4 shows a computed tomography device.

FIG. 4 shows the computed tomography device 1, having the radiation source 26 for generating radiation 27, the detector 28, the collimator K and the control unit 35, which is designed for field-oriented control of the second rotational movement of the first threaded spindle S1 and for field-oriented control of the second rotational movement of the second threaded spindle S2.

The computed tomography device 1 also has the gantry 20, the tunnel-shaped opening 9, the patient positioning apparatus 10 and the control apparatus 30. The gantry 20 has the stationary support frame 21, the tilt frame 22 and the rotor 24.

The tilt frame 22 is tiltably arranged on the stationary support frame 21 about a tilting axis relative to the stationary support frame 21 via a tilting positioning apparatus. The rotor 24 is rotatably arranged on the tilt frame 22 about the axis of rotation RA relative to the tilt frame 22 via a rotary bearing apparatus. The axis of rotation RA is perpendicular to the tilt axis.

The patient 13 can be inserted into the tunnel-shaped opening 9. The acquisition region 4 is located in the tunnel-shaped opening 9. In the acquisition region 4, the region N of the patient 13 to be imaged can be positioned in such a way that the radiation 27 can pass from the radiation source 26 to the region to be imaged and, after interaction with the region to be imaged, can reach the radiation detector 28.

The patient positioning apparatus 10 has the positioning base 11 and the positioning plate 12 for positioning the patient 13. The positioning plate 12 is arranged on the positioning base 11 so as to be moveable relative to the positioning base 11 in such a way that the positioning plate 12 can be inserted into the acquisition region 4 in a longitudinal direction of the positioning plate 12.

The control apparatus 30 is designed to receive the projection data acquired by the detector. The control apparatus 30 is designed to control the computed tomography device 1. The control apparatus 30 has the control unit 35, the computer-readable medium 32 and the processor system 36. The control apparatus 30, in particular, the control unit 35, is formed by a data processing system which has a computer.

The control apparatus 30 has the image reconstruction facility 34. By way of the image reconstruction facility 34, a medical image-data record can be reconstructed on the basis of the projection data.

The computed tomography device 1 has an input apparatus 38 and an output apparatus 39, which are each connected to the control apparatus 30. The input apparatus 38 is designed for inputting control information, e.g. image reconstruction parameters, examination parameters or the like. The output apparatus 39 is designed in particular for outputting control information, images, and/or acoustic signals.

The invention was illustrated and described herein before in detail with reference to example embodiments. It is understood that in particular the description with reference to the figures is for illustrative purposes only and shall not be interpreted in a limiting sense. Variations and combinations may be derived from the information disclosed herein before by the skilled person without departing form the scope or core ideas of present the invention, which are in particular reflected in the appended claims.

Although the invention has been illustrated in greater detail using the example embodiments, the invention is not limited by the disclosed examples, and a person skilled in the art can derive other variations therefrom without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for capturing projection data with a computed tomography device, the computed tomography device including a radiation source for generating radiation, a detector, and a collimator including a first diaphragm jaw and a second diaphragm jaw, the method comprising:
    positioning the first diaphragm jaw, the positioning the first diaphragm jaw comprising converting a first rotational movement of a first threaded spindle into a first translational movement of the first diaphragm jaw via a first threaded drive;
    positioning the second diaphragm jaw, the positioning the second diaphragm jaw comprising converting a first rotational movement of a second threaded spindle into a first translational movement of the second diaphragm jaw via a second threaded drive, wherein the positioning the first diaphragm jaw and the positioning the second diaphragm jaw set a layer collimation of a fan beam of the radiation via the first diaphragm jaw and the second diaphragm jaw;
    capturing the projection data of a region of a patient to be imaged via the detector while rotating the detector and the radiation source in a plane of rotation about an axis of rotation and while moving the region of the patient to be imaged relative to the plane of rotation, wherein the fan beam penetrates the region of the patient to be imaged and strikes the detector; and
    moving at least one of the first diaphragm jaw or the second diaphragm jaw during the capturing of the projection data to dynamically adjust a position of a boundary surface of the fan beam to a position of a boundary surface of the region of the patient to be imaged, such that penetration of the patient by the fan beam outside the region to be imaged is essentially avoided.

2. The method of claim 1, wherein, during the capturing of the projection data, the layer collimation of the fan beam of the radiation is kept constant for at least one half of a revolution of the detector and the radiation source about the axis of rotation.

3. The method of claim 2, wherein the position of a boundary surface of the fan beam is dynamically adjusted to the position of the boundary surface of the region of the patient to be imaged, until the fan beam is completely suppressed by the first diaphragm jaw and the second diaphragm jaw.

4. The method of claim 2, wherein the moving at least one of the first diaphragm jaw and the second diaphragm jaw takes place at a speed of at least 150 millimeters per second.

5. The method of claim 2, wherein at least one of:
the moving of the first diaphragm jaw includes a second rotational movement of the first threaded spindle being converted into a second translational movement of the first diaphragm jaw via the first threaded drive; or
the moving of the second diaphragm jaw includes a second rotational movement of the second threaded spindle being converted into a second translational movement of the second diaphragm jaw via the second threaded drive.

6. The method as claimed in claim 5, wherein at least one of:
the first rotational movement of the first threaded spindle and the second rotational movement of the first threaded spindle are driven via a first stepper motor; or
the first rotational movement of the second threaded spindle and the second rotational movement of the second threaded spindle are driven via a second stepper motor.

7. The method of claim 1, wherein the position of the boundary surface of the fan beam is dynamically adjusted to the position of the boundary surface of the region of the patient to be imaged, until the fan beam is completely suppressed by the first diaphragm jaw and the second diaphragm jaw.

8. The method of claim 1, wherein the moving at least one of the first diaphragm jaw and the second diaphragm jaw takes place at a speed of at least 150 millimeters per second.

9. The method of claim 1, wherein at least one of:
the moving of the first diaphragm jaw comprises a second rotational movement of the first threaded spindle being converted into a second translational movement of the first diaphragm jaw via the first threaded drive; or
the moving of the second diaphragm jaw comprises a second rotational movement of the second threaded spindle being converted into a second translational movement of the second diaphragm jaw via the second threaded drive.

10. The method as claimed in claim 9, wherein at least one of:
the first rotational movement of the first threaded spindle and the second rotational movement of the first threaded spindle are driven via a first stepper motor; or
the first-rotational movement of the second threaded spindle and the second rotational movement of the second threaded spindle are driven via a second stepper motor.

11. The method of claim 10, wherein at least one of:
the second rotational movement of the first threaded spindle is controlled in a field-oriented manners; or
the second rotational movement of the second threaded spindle is controlled in a field-oriented manner.

12. The method of claim 9, wherein at least one of
the second rotational movement of the first threaded spindle is controlled in a field-oriented manners; or
the second rotational movement of the second threaded spindle is controlled in a field-oriented manner.

13. A computed tomography device, comprising:
a radiation source to generate radiation;
a detector; and
a collimator including a first diaphragm jaw, a second diaphragm jaw, a first threaded spindle, a first threaded drive, a second threaded spindle, and a second threaded drive,
wherein the collimator is configured to position the first diaphragm jaw by converting a first rotational movement of the first threaded spindle into a first translational movement of the first diaphragm jaw via the first threaded drive and to position the second diaphragm jaw by converting a first rotational movement of the second threaded spindle into a first translational movement of the second diaphragm jaw via the second threaded drive, the first diaphragm jaw and the second diaphragm jaw being configurable to set a layer collimation of a fan beam of the radiation,
the detector is configured to capture projection data of a region of a patient to be imaged while rotating the detector and the radiation source in a plane of rotation about an axis of rotation and while moving the region of the patient to be imaged relative to the plane of rotation, wherein the fan beam is configured to penetrate the region of the patient to be imaged and strike the detector, and
the collimator is configured to move at least one of the first diaphragm jaw or the second diaphragm jaw during the capture of the projection data to dynamically adjust a position of a boundary surface of the fan beam to a position of a boundary surface of the region of the patient to be imaged, such that penetration of the patient by the fan beam outside the region to be imaged is essentially avoided.

14. The computed tomography device of claim 13, wherein the collimator is configured, during the capture of the projection data, to keep the layer collimation of the fan beam of the radiation constant for at least one half of a revolution of the detector and the radiation source about the axis of rotation.

15. The computed tomography device of claim 14, wherein the collimator is configured to dynamically adapt the position of the boundary surface of the fan beam to the position of the boundary surface of the region of the patient to be imaged, until the fan beam is completely suppressed by the first diaphragm jaw and the second diaphragm jaw.

16. The computed tomography device of claim 13, wherein the collimator is configured to dynamically adapt the position of the boundary surface of the fan beam to the position of the boundary surface of the region of the patient to be imaged, until the fan beam is completely suppressed by the first diaphragm jaw and the second diaphragm jaw.

17. The computed tomography device of claim 13, wherein the collimator is configured to move at least one of the first diaphragm jaw or the second diaphragm jaw, at a speed of at least 150 millimeters per second.

18. The computed tomography device of claim 13, wherein at least one of:
the first threaded drive is configured to convert a second rotational movement of the first threaded spindle into a second translational movement of the first diaphragm jaw, to move the first diaphragm jaw; or
the second threaded drive is configured to convert a second rotational movement of the second threaded spindle into a second translational movement of the second diaphragm jaw, to move the second diaphragm jaw.

19. The computed tomography device of claim 18, wherein at least one of:
a thread pitch of the first threaded spindle is at least 3 millimeters per revolution; or a thread pitch of the second threaded spindle is at least 3 millimeters per revolution.

20. The computed tomography device of claim 18, wherein at least one of:
the collimator includes a first stepper motor to drive the first rotational movement of the first threaded spindle and the second rotational movement of the first threaded spindle; or
the collimator includes a second stepper motor to drive the first rotational movement of the second threaded spindle and the second rotational movement of the second threaded spindle.

21. The computed tomography device of claim 18, further comprising:
a control unit designed for at least one of field-oriented control of the second rotational movement of the first threaded spindle or field-oriented control of the second rotational movement of the second threaded spindle.

* * * * *